United States Patent [19]

Gilman et al.

[11] 4,165,378
[45] Aug. 21, 1979

[54] GUANIDINE DERIVATIVES OF IMIDAZOLES AND THIAZOLES

[75] Inventors: David J. Gilman, Macclesfield; James M. Wardleworth, Wilmslow, both of England; Tobias O. Yellin, Wallingford, Pa.

[73] Assignee: ICI Americas Inc., Wilmington, Del.

[21] Appl. No.: 897,912

[22] Filed: Apr. 19, 1978

[51] Int. Cl.$^2$ ................. C07D 277/38; C07D 233/88; A61K 31/425; A61K 31/415

[52] U.S. Cl. ................. 424/270; 424/273 R; 260/306.8 R; 260/326 S; 260/326 N; 548/337

[58] Field of Search ................. 260/306.8 R; 424/270, 424/273

[56] References Cited

U.S. PATENT DOCUMENTS

| | | | |
|---|---|---|---|
| 3,876,647 | 4/1975 | Durant et al. | 424/263 |
| 3,897,444 | 7/1975 | Durant et al. | 260/306.8 R |
| 3,905,984 | 9/1975 | Durant et al. | 260/294.84 |
| 3,920,822 | 11/1975 | Durant et al. | 424/263 |
| 3,932,427 | 1/1976 | Durant et al. | 260/295 E |
| 3,950,333 | 4/1976 | Durant et al. | 260/302 A |
| 3,950,353 | 4/1976 | Durant et al. | 260/307 R |
| 3,975,530 | 8/1976 | Durant et al. | 424/270 |
| 4,018,391 | 4/1977 | Durant et al. | 424/269 |
| 4,018,928 | 4/1977 | Durant et al. | 424/263 |
| 4,018,931 | 4/1977 | Durant | 424/269 |
| 4,022,797 | 5/1977 | Durant et al. | 260/302 R |
| 4,038,408 | 7/1977 | Durant et al. | 424/270 |
| 4,049,672 | 9/1977 | Durant et al. | 548/342 |
| 4,053,473 | 10/1977 | Durant et al. | 548/329 |
| 4,062,863 | 12/1977 | Ganellin et al. | 260/306.8 R |

FOREIGN PATENT DOCUMENTS

| | | |
|---|---|---|
| 832660 | 2/1976 | Belgium . |
| 832661 | 2/1976 | Belgium . |
| 832662 | 2/1976 | Belgium . |
| 832663 | 2/1976 | Belgium . |
| 832664 | 2/1976 | Belgium . |
| 832665 | 2/1976 | Belgium . |
| 841526 | 11/1976 | Belgium . |
| 843814 | 11/1976 | Belgium . |
| 843839 | 1/1977 | Belgium . |
| 843840 | 1/1977 | Belgium . |
| 844503 | 1/1977 | Belgium . |
| 844504 | 1/1977 | Belgium . |
| 846452 | 3/1977 | Belgium . |
| 2604056 | 5/1976 | Fed. Rep. of Germany . |
| 1307539 | 2/1973 | United Kingdom . |
| 1305546 | 2/1973 | United Kingdom . |
| 1305548 | 2/1973 | United Kingdom . |
| 1305549 | 2/1973 | United Kingdom . |
| 1338169 | 11/1973 | United Kingdom . |
| 1341375 | 12/1973 | United Kingdom . |
| 1341376 | 12/1973 | United Kingdom . |
| 1395929 | 5/1975 | United Kingdom . |
| 1397436 | 6/1975 | United Kingdom . |
| 1398426 | 6/1975 | United Kingdom . |
| 1399283 | 7/1975 | United Kingdom . |
| 1400319 | 7/1975 | United Kingdom . |
| 1419994 | 1/1976 | United Kingdom . |
| 1421792 | 1/1976 | United Kingdom . |
| 1421999 | 1/1976 | United Kingdom . |
| 1422408 | 2/1976 | United Kingdom . |
| 1431589 | 4/1976 | United Kingdom . |
| 1493931 | 11/1977 | United Kingdom . |
| 1496787 | 5/1978 | United Kingdom . |
| 1497260 | 5/1978 | United Kingdom . |

*Primary Examiner*—Mark L. Berch

[57] ABSTRACT

The invention relates to guanidine derivatives of imidazoles and thiazoles which are histamine H-2 antagonists and which inhibit the secretion of gastric acid, to methods for their manufacture, to pharmaceutical compositions containing them and to methods of using such guanidine derivatives and compositions. The guanidine derivatives are of the general formula I:

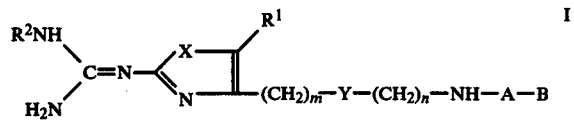

in which X is S or NH, Y is O, S, or SO, m is 1 to 4 and n is suitably 1 to 4, $R^1$ is hydrogen, halogen or alkyl, $R^2$ is hydrogen, alkyl, alkanoyl or aroyl, A is a 3,4-dioxocyclobuten-1,2-diyl radical or C=Z in which Z is O, S, NCN, NNO$_2$, CHNO$_2$, NCONH$_2$, C(CN)$_2$, NCOR$^3$, NCO$_2$R$^3$, NSO$_2$R$^3$ or NR$^4$ in which R$^3$ is alkyl or aryl and R$^4$ is hydrogen or alkyl, B is alkoxy or alkylthio or NR$^5$R$^6$ in which R$^5$ and R$^6$ are independently hydrogen, alkyl, alkenyl, cycloalkyl, hydroxyalkyl, alkoxyalkyl, alkylaminoalkyl or dialkylaminoalkyl; and the salts thereof.

19 Claims, No Drawings

GUANIDINE DERIVATIVES OF IMIDAZOLES AND THIAZOLES

This invention relates to guanidine derivatives which are histamine H-2 antagonists and which inhibit gastric acid secretion.

It is postulated that the physiologically active compound histamine, which occurs naturally within the animal body, is able to combine, in the course of exerting its activity, with certain specific receptors of which there are at least two distinct and separate types. The first has been named the H-1 receptor (Ash and Schild, *Brit. J. Pharmac.*, 1966, 27, 427) and the action of histamine at this receptor is blocked (antagonized) by classical "anthistamine" drugs such as mepyramine (pyrilamine). The second histamine receptor has been named the H-2 receptor (Blac et al., Nature, 1972, 236, 385) and the action of histamine at this receptor is blocked by drugs such as cimetidine. It is known that one of the results of the blockage of the action of histamine at the H-2 receptor is the inhibition of the secretion of gastric acid and a compound which possesses this ability is therefore useful in the treatment of peptic ulcers and other conditions caused or exacerbated by gastric acidity, including stress ulcers and gastrointestinal bleeding due to trauma.

In U.K. Pat. Nos. 1,338,169 and 1,397,436 there are described histamine H-2 receptor antagonists which are imidazole and thiazole derivatives having a side chain in the 4-position, to the end of which is attached, for example, a urea, thiourea, guanidine or N-cyanoguanidine. It has now been discovered that if an optionally-substituted guanidino radical is inserted in the 2-position of such compounds, there are produced compounds which are potent histamine H-2 receptor antagonists.

According to the invention there is provided a guanidine derivative of the formula I:

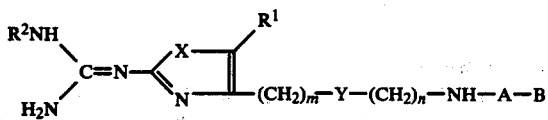

in which X is a sulphur atom or an NH radical; Y is an oxygen or sulphur atom, or a sulphinyl radical; m is 1 to 4 and n is 1 to 4, provided that when Y is an oxygen atom or a sulphinyl radical n is 2 to 4; $R^1$ is a hydrogen or halogen atom or an alkyl radical of 1 to 6 carbon atoms; $R^2$ is a hydrogen atom, an alkyl radical of 1 to 10 carbon atoms, an alkanoyl radical of 1 to 6 carbon atoms or an aroyl radical of 7 to 11 carbon atoms; A is a 3,4-dioxocyclobuten-1,2-diyl radical or a radical of the formula C=Z in which Z is an oxygen or sulphur atom or a radical of the formula NCN, NNO$_2$, CHNO$_2$, NCONH$_2$, C(CN)$_2$, NCOR$^3$, NCO$_2$R$^3$, NSO$_2$R$^3$ or NR$^4$ in which $R^3$ is a alkyl radical of 1 to 6 carbon atoms or an aryl radical of 6 to 12 carbon atoms and $R^4$ is a hydrogen atom or an alkyl radical of 1 to 6 carbon atoms; B is an alkoxy or alkylthio radical of 1 to 6 carbon atoms or a radical of the formula NR$^5$R$^6$ in which $R^5$ and $R^6$, which may be the same or different, are hydrogen atoms, alkyl radicals of 1 to 10 carbon atoms, alkenyl radicals of 3 to 10 carbon atoms in which the double bond is separated from the nitrogen atom of NR$^5$R$^6$ by at least one carbon atom, cycloalkyl radicals of 3 to 8 carbon atoms, (primary hydroxy)alkyl radicals of 2 to 6 carbon atoms in which the oxygen atom is separated from the nitrogen atom of NR$^5$R$^6$ by at least two carbon atoms, alkoxyalkyl radicals of 3 to 10 carbon atoms in which the oxygen atom is separated from the nitrogen atom of NR$^5$R$^6$ by at least two carbon atoms, alkylaminoalkyl radicals of 3 to 10 carbon atoms in which the nitrogen atom is separated from the nitrogen atom of NR$^5$R$^6$ by at least two carbon atoms; or dialkylaminoalkyl radicals of 4 to 10 carbon atoms in which the nitrogen atom is separated from the nitrogen atom of NR$^5$R$^6$ by at least two carbon atoms; and the pharmaceutically acceptable acid-addition salts thereof.

It is to be understood that, in the above formula I and throughout this specification, although the double bonds in both side chains have been inserted in particular positions, various other tautomeric forms are possible, and this invention includes such tautomeric forms within its scope, both in terms of the compound of the invention and in terms of the manufacturing processes.

The term "halogen" as used herein means that recognized group of halogens which have an atomic weight of at most 127 and are chlorine, fluorine, bromine and iodine.

A particular value for $R^1$ when it is a halogen atom o an alkyl radical is a bromine atom or a methyl radical.

A particular value for $R^2$ when it is an alkyl, alkanoyl or aroyl radical is a methyl, n-butyl, acetyl, propionyl or benzoyl radical.

A particular value for $R^3$ is a methyl or p-tolyl radical.

A particular value for $R^4$ is a methyl radical.

A particular value for B when it is an alkoxy or alkylthio radical is a methoxy, ethoxy or methylthio radical.

A particular value for $R^5$ or $R^6$ when it is an alkyl, alkenyl, cycloalkyl, (primary hydroxy)alkyl, alkoxyalkyl or di-alkylaminoalkyl radical is a methyl, ethyl, n-propyl, isopropyl, n-hexyl, allyl, cyclohexyl, 2-hydroxyethyl, 3-hydroxypropyl, 2-methoxyethyl or 2-dimethylaminoethyl radical.

The following are 8 preferred features of the guanidine derivative of the formula I. When any one of these 8 features is taken, either singly or in combination, with the other general features of the guanidine derivatives of the formula I listed above, there are obtained preferred sub-groups of compounds within the above general definition.

1. X is a sulphur atom.
2. $R^1$ is a hydrogen atom.
3. $R^2$ is a hydrogen atom or an alkyl radical of 1 to 6 carbon atoms.
4. B is a radical of the formula NR$^5$R$^6$ in which $R^6$ is a hydrogen atom.
5. B is an alkoxy radical of 1 to 4 carbon atoms or an alkylthio radical of 1 to 4 carbon atoms.
6. A is a 3,4-dioxocyclobuten-1,2-diyl radical or a radical of the formula C=Z in which Z is an oxygen or sulphur atom or a radical of the formula NCN, NNO$_2$ or CHNO$_2$.
7. Y is a sulphur atom and m is 1 and n is 2.
8. B is a radical of the formula NR$^5$R$^6$ in which $R^5$ is a methyl radical and $R^6$ is a hydrogen atom.

The following group of compounds is particularly preferred:

2-guanidino-4-[2-(2-cyano-3-ethylguanidino)ethylthiomethyl]thiazole;

2-guanidino-4-[2-(2-cyano-3-methylguanidino)ethylthiomethyl]thiazole;

2-guanidino-4-[2-(2-nitroguanidino)ethylthiomethyl]-
thiazole;
2-guanidino-4-[2-(2-cyanoguanidino)ethylthiomethyl]-
thiazole;
2-guanidino-4-[2-(2-cyano-3-(2-hydroxyethyl)-
guanidino)ethylthiomethyl]thiazole;
and the pharmaceutically acceptable acid-addition salts thereof.

A suitable pharmaceutically acceptable acid-addition salt of the guanidine derivative of the invention is, for example, a salt formed with hydrochloric, hydrobromic, phosphoric, sulphuric, acetic, citric or maleic acid.

All of the compounds within the scope of the present invention can be prepared in accordance with the principles, processes and techniques illustrated in the following described processes and Examples. In the following described processes X, Y, m, n, A, B, $R^1$, $R^2$, $R^3$, $R^4$, $R^5$ and $R^6$ have the meanings stated above unless indicated otherwise.

The processes that can be used to prepare the compounds of this invention are as follows:

(a) reaction of a compound of the formula II:

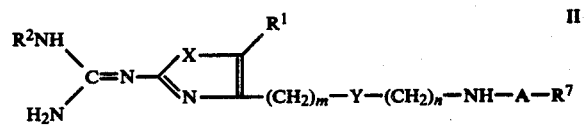

in which $R^7$ is a displaceable radical, with a compound of the formula B—H;

(b) for those compounds in which A is a radical of the formula C=Z in which Z is a sulphur or oxygen atom and B is a radical of the formula $NR^5R^6$ in which $R^6$ is a hydrogen atom and $R^5$ has the value stated above other than a hydroxyalkyl or alkylaminoalkyl radical, reaction of a compound of the formula III:

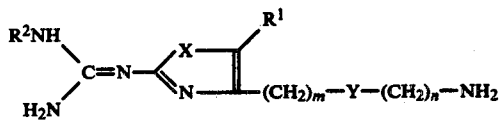

with a compound of the formula $R^8N=C=D$ in which D is an oxygen or sulphur atom and $R^8$ is a hydrogen atom or an alkyl, alkenyl, cycloalkyl, alkoxyalkyl, or dialkylaminoalkyl radical, such as suitably methyl, ethyl, n-propyl, isopropyl, n-hexyl, allyl, cyclohexyl, 2-methoxyethyl or 2-dimethylaminoethyl, depending on the identity of $R^5$ desired;

(c) for those compounds in which A is a radical of the formula C=Z in which Z is a radical of the formula NCN and B is a radical of the formula $NR^5R^6$ in which $R^5$ and $R^6$ are hydrogen atoms, reaction of a compound of the formula III with dicyanimide or a salt thereof;

(d) reaction of a compound of the formula III with a compound of the formula IV:

$$R^7-A-B \qquad\qquad IV$$

in which $R^7$ is a displaceable radical;

(e) for those compounds in which $R^2$ is a hydrogen atom or an alkyl radical, A is a radical of the formula C=Z in which Z is a radical of the formula $NCONH_2$ and B is a radical of the formula $NR^5R^6$, hydrolysis of a compound of the formula I in which $R^2$ is a hydrogen atom or an alkyl radical, A is a radical of the formula C=Z in which Z is a radical of the formula NCN and B is a radical of the formula $NR^5R^6$;

(f) for those compounds in which $R^2$ is an alkanoyl or aroyl radical, reaction of a compound of the formula I in which $R^2$ is a hydrogen atom with an acid, or an acylating agent derived from an acid, of the formula $R^9CO_2H$ in which $R^9$ is a hydrogen atom, an alkyl radical of 1 to 9 carbon atoms or an aryl radical of 6 to 10 carbon atoms;

(g) for those compounds in which $R^2$ is a hydrogen atom or an alkyl radical and B is a radical of the formula $NR^5R^6$, hydrolysis of a compound of the formula V:

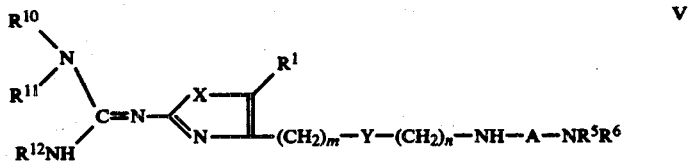

in which $R^{10}$ is a hydrogen atom or an alkyl radical of 1 to 10 carbon atoms, one of $R^{11}$ and $R^{12}$ is an alkanoyl radical of 1 to 6 carbon atoms or an aroyl radical of 7 to 11 carbon atoms and the other is a hydrogen atom;

(h) for those compounds in which Y is a sulphinyl radical, oxidation of a compound of the formula I in which Y is a sulphur atom;

(i) for those compounds in which A is a radical of the formula C=Z in which Z is an oxygen atom and B is a radical of the formula $NR^5R^6$, hydrolysis of a compound of the formula VI:

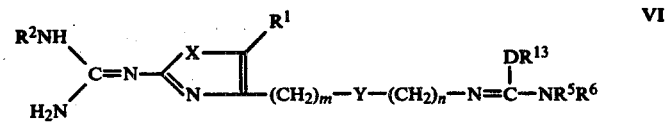

in which D is an oxygen or sulphur atom and $R^{13}$ is an alkyl radical of 1 to 6 carbon atoms;

(j) for those compounds in which A is a radical of the formula C=Z in which Z is a radical of the formula $NR^4$ and B is an alkoxy or alkylthio radical of 1 to 6 carbon atoms, alkylation of a compound of the formula VII:

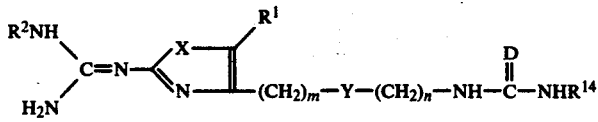

VII in which D is an oxygen or sulphur atom and $R^{14}$ is a hydrogen atom or an alkyl radical of 1 to 6 carbon atoms;

(k) for those compounds in which Y is a sulphur or oxygen atom, and B is a radical of the formula $NR^5R^6$, reaction of a compound of the formula VIII:

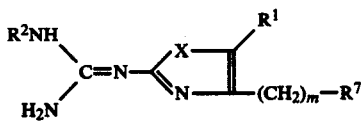

VIII in which $R^7$ is a displaceable atom or radical, with a compound of the formula IX:

$$H-D-(CH_2)_n-A-NR^5R^6 \qquad IX$$

in which D is an oxygen or sulphur atom;

(l) for those compounds in which B is a radical of the formula $NR^5R^6$ in which at least one of $R^5$ and $R^6$ is other than a hydrogen atom, reaction of a compound of the formula X:

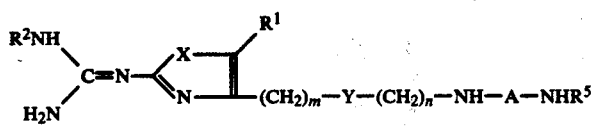

X with an alkylating agent derived from $R^{15}$—H in which $R^{15}$ is an alkyl, alkenyl, cycloalkyl, hydroxyalkyl, alkoxyalkyl, alkylaminoalkyl or dialkylaminoalkyl radical such as methyl, ethyl, n-propyl, isopropyl, n-hexyl, hydroxypropyl, allyl, cyclohexyl, 2-methoxyethyl, 2-dimethylaminoethyl or ethylaminoethyl, depending on the identity of B desired;

(m) for those compounds in which A is a radical of the formula C=Z in which Z is a radical of the formula NCN, $NCOR^3$, $NCO_2R^3$ or $NSO_2R^3$ and B is a radical of the formula $NR^5R^6$, reaction of a compound of the formula XI:

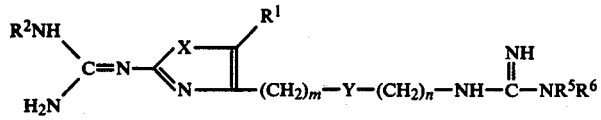

XI with a compound of the formula $R^7CN$, $R^7COR^3$, $R^7CO_2R^3$ or $R^7SO_2R^3$ in which $R^7$ is a displaceable atom or radical;

(n) for those compounds in which A is a radical of the formula C=Z in which Z is a radical of the formula NCN, $NCOR^3$, $NCO_2R^3$ or $NSO_2R^3$, and B is a radical of the formula $NR^5R^6$ in which $R^6$ is a hydrogen atom, reaction of a compound of the formula XII:

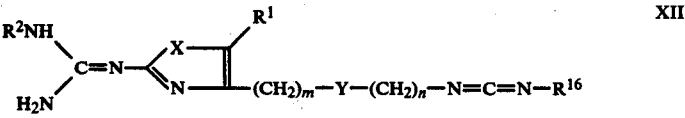

XII in which $R^{16}$ is either a radical of the formula $R^5$ or a radical of the formula CN, $COR^3$, $CO_2R^3$ or $SO_2R^3$, with a compound of the formula $H_2N-R^{17}$ in which $R^{17}$ is either a radical of the formula CN, $COR^3$, $CO_2R^3$ or $SO_2R^3$, or a radical of the formula $R^5$ respectively;

(o) for those compounds in which A is a radical of the formula C=Z in which Z is a radical of the formula NCN, $NCOR^3$, $NCO_2R^3$ or $NSO_2R^3$ and B is a radical of the formula $NR^5R^6$ in which $R^6$ is a hydrogen atom, reaction of a compound of the formula III with a compound of the formula XIII:

$$R^5N=C=N-R^{18} \qquad XIII$$

in which $R^{18}$ is a radical of the formula CN, $COR^3$, $CO_2R^3$ or $SO_2R^3$;

(p) for those compounds in which A is a radical of the formula C=Z in which Z is a radical of the formula NCN, $NCONH_2$, $NCOR^3$, $NCO_2R^3$, $NSO_2R^3$ or $NR^4$ and B is a radical of the formula $NR^5R^6$, reaction of a compound of the formula XIV:

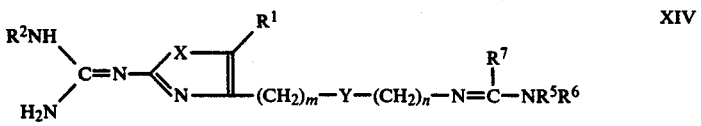

XIV in which $R^7$ is a displaceable radical with a compound of the formula $H_2NCN$, $H_2NCONH_2$, $H_2NCOR^3$, $H_2NCO_2R^3$, $H_2NSO_2R^3$, or $H_2NR^4$;

(q) for those compounds in which A is a radical of the formula C=Z in which Z is a radical of the formula NCN, NCOR$^3$, NCO$_2$R$^3$ or NSO$_2$R$^3$, and B is a radical of the formula NR$^5$R$^6$, reaction of a compound of the formula XV:

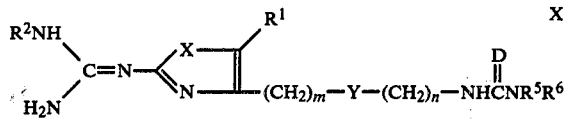   XV in which D is a sulphur or oxygen atom with a compound of the formula $H_2NCN$, $H_2NCOR^3$, $H_2NCO_2R^3$ or $H_2NSO_2R^3$; or (r) for those compounds in which B is a radical of the formula NR$^5$R$^6$, reaction of a molecule of the formula XVI,

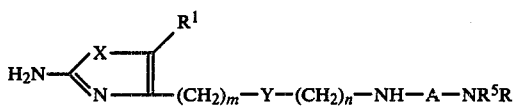   XVI with a molecule of the formula XVII:

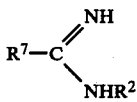   XVII in which $R^7$ is a displaceable radical.

When the process of the invention manufactures the compound of the formula I in the form of the free base and an acid-addition salt is required, the compound of the formula I in the free base form is reacted with an acid which affords a pharmaceutically acceptable anion.

Process (a) described above may be carried out using an excess of B-H, that is using an excess of the amine R$^5$R$^6$NH, optionally in the presence of a diluent or solvent such as water, methanol, ethanol or pyridine, or using an excess of the alcohol R$^{13}$OH or the thiol R$^{13}$SH in which R$^{13}$ is an alkyl radical of 1 to 6 carbon atoms, preferably in the form of a salt such as the sodium salt in the same alcohol or thiol as diluent or solvent. In process (a) R$^7$ is preferably an alkoxy or alkylthio radical, for example the methoxy, ethoxy or methylthio radical, or an amino radical. The process may be accelerated or completed by the application of heat, for example by boiling the reaction mixture.

Process (b) described above may be carried out using an excess of the isocyanate or isothiocyanate R$^8$N=C=D. When D is a sulphur atom, the reaction is preferably carried out in a diluent or solvent such as methanol or ethanol. When D is an oxygen atom, a non-alcoholic diluent or solvent must be used.

Process (c) described above may be carried out using the sodium salt of dicyanimide in a diluent or solvent such as n-butanol. The reaction may be accelerated or completed by the application of heat, for example by heating to the boiling point of the reaction mixture.

Process (d) described above may be carried out using an excess of the compound of the formula IV in a diluent or solvent such as methanol, ethanol or acetonitrile.

In process (d) $R^7$ is preferably an alkoxy or alkylthio radical, for example a methoxy, ethoxy or methylthio radical. The reaction may be accelerated or completed by the application of heat, for example by heating to the boiling point of the reaction mixture.

Process (e) described above may be carried out using a dilute mineral acid, for example dilute hydrochloric acid, in a diluent or solvent such as water. The reaction may be accelerated or completed by application of heat, for example by heating to the boiling point of the reaction mixture.

Process (f) described above may be carried ot in an inert diluent or solvent, and in the presence of a base, at or below room temperature. The diluent or solvent is preferably pyridine which also acts as the base. The reaction is preferably carried out using the acid chloride or the acid anhydride as the acylating agent.

In process (g) described above R$^{11}$ or R$^{12}$ is preferably an acetyl, propionyl or benzoyl radical. The process may be carried out using a dilute base such as sodium hydroxide in a diluent or solvent such as aqueous methanol or aqueous ethanol.

Process (h) described above may be carried out using a mild oxidizing agent such as sodium metaperiodate in a diluent or solvent such as aqueous methanol or aqueous ethanol.

Process (i) described above may be carried out using a mild aqueous base, for example aqueous sodium carbonate. The reaction may be accelerated or completed by the application of heat, for example by heating to 100° C.

In process (j) described above, when D is a sulphur atom the reaction is preferably carried out using an alkyl (C$_1$ to C$_4$) halide, for example methyl iodide in a diluent or solvent such as ethanol. The reaction may be accelerated or completed by the application of heat.

In process (k) described above $R^7$ is preferably a halogen atom, for example a chlorine or bromine atom or a triphenylphosphonium radical.

In process (l) described above the alkylating agent derived from R$^{15}$—H is preferably the corresponding halide such as methyl iodide or allyl chloride.

In process (m) described above the displaceable atom or radical is preferably a halogen atom.

In process (p) described above $R^7$ is preferably a halogen atom or an alkoxy or alkylthio radical containing 1 to 4 carbon atoms.

In process (r) described above $R^7$ is preferably an alkoxy or alkylthio radical containing 1 to 4 carbon atoms.

When Y is a sulphur or oxygen atom the starting material of the formula III for use in process (b), (c), (d) or (o) may be suitably prepared by reaction of a dichloroketone of the formula ClCHR$^1$CO(CH$_2$)$_m$Cl with a compound of the formula XVIII:

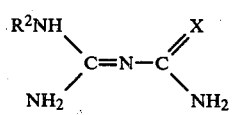   XVIII followed by reaction of the product, the compound of the formula XIX:

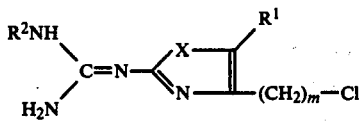

with a compound of the formula HD—$(CH_2)_n$—$NH_2$ in which D is an oxygen or sulphur atom, for example as set out in following Examples 1, 5 or 18.

The starting material of the formula III in which $R^1$ is a halogen atom may be prepared by halogenation of the compound of the formula III in which $R^1$ is a hydrogen atom using standard halogenation methods.

The starting material of the formula II for use in process (a) may be prepared by reaction of a compound of the formula III with a compound of the formula $R^7$—A—$R^7$, in which $R^7$ is a displaceable radical such as methoxy or methylthio, such as dimethyl (cyanoimido)dithiocarbonate, for example as set out in following Examples 1, 5, 17, 20 or 22.

The starting material of the formula VI for use in process (i) may be obtained by alkylation of the compound of the formula I in which A is a radical of the formula C=Z in which Z is an oxygen or sulphur atom, for example as set out in following Example 25.

The starting material of the formula XII for use in process (n) may be prepared, for example, by reaction of a compound of the formula XX:

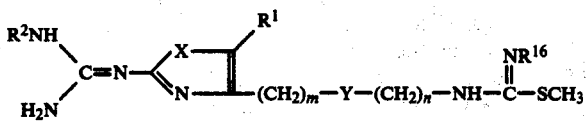

where $R^{16}$ is a radical as described above under process (n); with silver nitrate.

When X is sulphur atom the starting material of the formula XVI for use in process (r) may be prepared in the same way as for the starting material of the formula III, but using thiourea in place of the compound of the formula XVIII. One of the processes of the present invention is then performed on the product, the 2-aminothiazole derivative corresponding to the compound of the formula III, for example process (b), (c) or (d), to give the compound of the formula XVI. When X is an NH radical, the starting material of the formula XVI may be prepared by reaction of cyanamide with an aminoketone of the formula XXI:

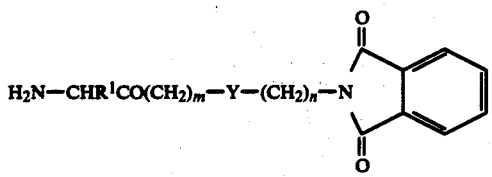

followed by removal of the phthalimido residue and elaboration of the side chain in the product, the 2-aminoimidazole derivative corresponding to the compound of the formula III.

The following examples will further serve to illustrate the present invention.

EXAMPLE 1

A suspension of 2-guanidino-4-[(2-aminoethyl)thiomethyl]thiazole hydrochloride (9.12 g.) in methanol (300 ml.) was treated with triethylamine (6.06 g.) to give a clear pale yellow solution. Dimethyl (cyanoimido)dithiocarbonate (4.38 g.) was added and the solution stirred overnight at room temperature. The mixture was poured into water and extracted with ethyl acetate to give a yellow gum. Trituration with acetone gave 2-guanidino-4-[2-(3-cyano-2-methylisothioureido)ethylthiomethyl]thiazole (7.3 g.) as a pink slid, m.p. 146°–148° C.

The 2-guanidino-4-[(2-aminoethyl)thiomethyl]thiazole hydrochloride used as starting material may be prepared as follows:

A suspension of amidinothiourea (16.8 g.) in acetone (75 ml.) was treated with 1,3-dichloroacetone (18 g.) in acetone (60 ml.). There was a slight exotherm and the crystalline suspension gradually changed to a fine white solid. After stirring overnight at room temperature the solid was filtered off and washed with acetone. Crystallization from ethanol gave 2-guanidino-4-chloromethylthiazole hydrochloride, m.p. 191°–193° C.

A solution of 2-aminoethanethiol hydrochloride (4.52 g.) in ethanol (40 ml.) was added portionwise at 0° C. to a solution of sodium ethoxide (prepared from 2 g. of sodium) in ethanol (60 ml.) under a nitrogen atmosphere. After stirring at 0° C. for 2 hours, a solution of 2-guanidino-4-chloromethylthiazole hydrochloride (4.54 g.) in ethanol (35 ml.) was added dropwise over 15 minutes while the temperature was maintained at 0°–2° C. After the addition was complete the reaction mixture was stirred at room temperature for 16 hours, filtered, and the filtrate acidified with concentrated hydrochloric acid. On standing 2-guanidino-4-[(2-aminoethyl)thiomethyl]thiazole hydrochloride precipitated as a white crystalline solid (4.56 g.), m.p. 268°–270° C. (decomposed).

EXAMPLE 2

A mixture of 2-guanidino-4-[2-(3-cyano-2-methylisothioureido)ethylthiomethyl]thiazole (1.1 g.) in ethanol (25 ml.) was treated with 70% w/v aqueous ethylamine (5 ml.) at room temperature. The mixture was stirred overnight at room temperature and the solution evaporated to dryness. The residue was crystallized from methanol to give 2-guanidino-4-[2-(2-cyano-3-ethylguanidino)ethylthiomethyl]thiazole (0.53 g.), m.p. 181°–182° C.

EXAMPLE 3

A mixture of 2-guanidino-4-[2-(3-cyano-2-methylisothioureido)ethylthiomethyl]thiazole (1 g.) and 30% w/v aqueous methylamine (5 ml.) in ethanol (25 ml.) was stirred for 5 hours at room temperature and the solution was then evaporated to dryness. The residual white foam was dissolved in acetone (10 ml.) and a solution of maleic acid (1 g.) in acetone (12 ml.) added. The precipitated white solid was filtered and crystallized from methanol to give 2-quanidino-4-[2-(2-cyano-3-methylguanidino)ethylthiomethyl]thiazole hydrogen maleate, m.p. 175°–177° C.

A purer product was obtained when 30% w/v ethanolic methylamine (17 ml.) was substituted for aqueous methylamine in the above reaction.

The following acid addition salts of the above product were obtained by conventional means:

| Salt | m.p. °C. | Recrystallization Solvent |
|---|---|---|
| Fumarate | 188–190 | Water |
| Succinate | 160–161 | Water |
| Hydrochloride | * | Ethanol |
| Hydrogen Tartrate | 67–70 | Water |

*Found: C, 32.8; H, 5.2; N, 30.6. $C_{10}H_{17}ClN_8S_2 \cdot H_2O$ requires C, 33.1; H, 5.0; N, 30.6%.

EXAMPLE 4

A suspension of 2-guanidino-4-[(2-aminoethyl)thiomethyl]thiazole hydrochloride (1.52 g.) in methanol (30 ml.) was treated with triethylamine (1.01 g.) to give a pale yellow solution. Methyl isothiocyanate (0.365 g.) was added and the solution stirred for 16 hours at room temperature. Evaporation of the solvent gave a gum which was dissolved in acetone (20 ml.) and treated with maleic acid (1 g.) in acetone (20 ml.). The precipitate was filtered off and recrystallized from ethanol to give 2-guanidino-4-[2-(3-methylthioureido)ethylthiomethyl]thiazole hydrogen maleate as a pale brown solid (0.420 g.). Found: C, 37.4; H, 4.7; N, 19.8; S, 22.7. $C_{13}H_{20}N_6S_3O_4$ requires C, 37.14; H, 4.76; N, 20.00; S, 22.85%.

The n.m.r. spectrum in $d_6$ dimethyl sulphoxide using tetramethylsilane as an internal standard ($\delta=0$) had the following resonances ($\delta$): 2.65 (2H, multiplet); 2.85 (3H, doublet); 3.60 (2H, multiplet); 3.8 (2H, singlet); 6.1 (2H, singlet); 7.1 (1H, singlet; 7.55 (2H, broad singlet); 8.1 (4H, broad singlet).

EXAMPLE 5

A solution of 2-guanidino-4-[(3-aminopropyl)thiomethyl)]thiazole hydrochloride (1.64 g.) and triethylamine (1.01 g.) in cold methanol (20 ml.) was treated with dimethyl (cyanoimido) dithiocarbonate (0.73 g.) and the solution stirred for 16 hours at room temperature. 33% w/v ethanolic methylamine (12 ml.) was added and the mixture stirred at room temperature for 18 hours. The solution was evaporated to give a brown gum which was applied to Merck 60 F-254 preparative thin layer chromatography plates and eluted with ethyl acetate/ammonia (s.g. 0.880)/ethanol 6:1:1 v/v/v. The pale yellow oil was converted to the hydrogen maleate salt and the product recrystallized from methanol to give 2-guanidino-4-[3-(2-cyano-3-methylguanidino)propylthiomethyl]thiazole hydrogen maleate, m.p. 175°–177° C.

The starting material may be prepared as follows:

3-Aminopropanethiol hydrochloride (2.54 g.) in ethanol (20 ml.) was added to a solution of sodium ethoxide (1 g. Na in 25 ml. ethanol) at 0° C. under a nitrogen atmosphere. The suspension was stirred at 0° C. for 2 hours and a solution of 2-guanidino-4-chloromethylthiazole hydrochloride (2.27 g.) in ethanol (25 ml.) was then added. The suspension was allowed to reach room temperature and stirred for 16 hours. Filtration of the suspension and acidification of the filtrate with concentrated hydrochloric acid gave a precipitate of 2-guanidino-4-[(3-aminopropyl)thiomethyl]thiazole hydrochloride, m.p.>350° C.

EXAMPLE 6

2-Guanidino-4-[(2-aminoethyl)thiomethyl]thiazole hydrochloride (0.608 g.) in methanol (15 ml.) was treated with triethylamine (0.404 g.) and the solution stirred for 15 minutes before the addition of 2-methyl-1-nitroisothiourea (0.606 g.). The reaction mixture was heated on the steam bath for four hours. It was then evaporated to dryness and the residue taken up into small volume of ethanol and filtered. The ethanol filtrate was applied to Merck 60 F-254 preparative thin layer chromatography plates and eluted with ethyl acetate/ammonia (s.g. 0.880)/ethanol 6:1:1 v/v/v. The required product, obtained as a foam, was treated with an acetone solution of maleic acid which caused precipitation of a solid which was filtered and washed with acetone and methanol to give 2-guanidino-4-[2-(2-nitroguanidino)ethylthiomethyl]thiazole hydrogen maleate, m.p. 202°–206° C.

EXAMPLE 7

A mixture of 2-guanidino-4-[(2-aminoethyl)thiomethyl]thiazole hydrochloride (3.04 g.) n-butanol (30 ml.) was treated with triethylamine (2.02 g.) followed by sodium dicyanimide (0.89 g), and the resulting solution heated under reflux for 2.5 hours. The solution was evaporated to dryness to give a yellow gum which was purified by applying it to Merck 60 F-254 preparative thin layer chromatography plates and eluting with chloroform/methanol/ammonia (s.g. 0.880) 7:3:0.5 v/v/v. The resulting yellow gum was converted to the hydrogen maleate salt which was filtered and washed with boiling methanol to give 2-guanidino-4-[2-(2-cyanoguanidino)ethylthiomethyl]thiazole hydrogen maleate, m.p. 179°–181.5° C.

EXAMPLE 8

A mixture of 2-guanidino-4-[2-(2-cyano-3-methylguanidino)ethylthiomethyl]thiazole (1.0 g.), and 2.5 N hydrochloric acid (12 ml.) was heated for four minutes on the steam bath. On cooling a white solid precipitated which was applied to Merck 60 F-254 preparative thin layer chromatography plates and eluted with chloroform/methanol/ammonia (s.g. 0.880) 7:3:0.5 v/v/v. The yellow foam obtained was dissolved in methanol and methanolic hydrogen chloride added. The solution was evaporated to dryness and the residue crystallized from methanol to give 2-guanidino-4-[2-(2-carbamoyl-3-methylguanidino)ethylthiomethyl]thiazole hydrochloride, m.p. 148°–150° C.

EXAMPLE 9

The process described in Example 3 was repeated using an excess of the appropriate amine in place of methylamine in ethanol and the following compounds were thus obtained:

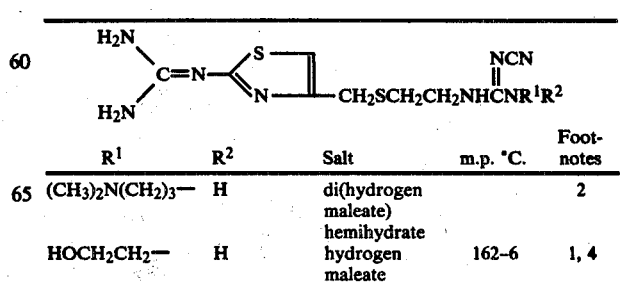

| $R^1$ | $R^2$ | Salt | m.p. °C. | Footnotes |
|---|---|---|---|---|
| $(CH_3)_2N(CH_2)_3-$ | H | di(hydrogen maleate) hemihydrate | | 2 |
| $HOCH_2CH_2-$ | H | hydrogen maleate | 162–6 | 1, 4 |

-continued $$H_2N\diagdown C=N-\underset{N}{\overset{S}{\diagup}}-CH_2SCH_2CH_2NH\overset{NCN}{\underset{\|}{C}}NR^1R^2$$

| $R^1$ | $R^2$ | Salt | m.p. °C. | Footnotes |
|---|---|---|---|---|
| $CH_3-$ | $CH_3-$ | free base | 166-8 | 1, 4 |
| $CH_3(CH_2)_5-$ | H | hydrogen maleate | | 1, 3 |

Footnotes
1. Product isolated by preparative thin layer chromatography on Merck 60 F-254 plates using ethyl acetate/ammonia (s.g. 0.880)/ethanol 6:1:1 v/v/v as developing solvent.
2. Found: C, 42.3; H, 5.45; N, 20.2. $C_{22}H_{33}N_9S_2O_8.O.5H_2O$ requires C, 42.2; H, 5.4; N, 20.2%.
3. Found: C, 45.8; H, 6.0; N, 22.5. $C_{19}H_{30}N_8S_2O_4$ requires C, 45.6; H, 6.0; N, 22.1%.
4. Recrystallized from ethanol.

EXAMPLE 10

A solution of 2-guanidino-4-[2-(3-cyano-2-methylisothioureido)ethylthiomethyl]thiazole (1.06 g.) in ethanol (25 ml.) was added to a stirred mixture of silver nitrate (0.60 g.), isopropylamine (5 ml.) and ethanol (20 ml.). The mixture was stirred at room temperature for 4 days, filtered, and the residue washed with methanol (10 ml.). The combined filtrates were evaporated to dryness, and the residual crude free base converted to the maleate salt. This was crystallized from methanol/toluene to give 2-guanidino-4-[2-(2-cyano-3-isopropylguanidino)ethylthiomethyl]thiazole hydrogen maleate, m.p. 162°-165° C. (decomposed).

EXAMPLE 11

A mixture of 2-methoxyethylamine (4 g.) and 2-guanidino-4-[2-(3-cyano-2-methylisothioureido)ethylthiomethyl]thiazole (1 g.) in methanol (10 ml.) was stirred at room temperature for 3 days. The mixture was evaporated to dryness, and the residual crude free base converted to the maleate salt, which was recrystallized from ethanol to give 2-guanidino-4-[2-(2-cyano-3-(2-methoxyethyl)guanidino)ethylthiomethyl]thiazole hydrogen maleate, m.p. 159°-161° C.

The above process was repeated using the appropriate amine in place of 2-methoxyethylamine and the following compounds were thus obtained as the hydrogen maleate salts $$H_2N\diagdown C=N-\underset{N}{\overset{S}{\diagup}}-CH_2SCH_2CH_2NH\overset{NCN}{\underset{\|}{C}}NHR$$

| R | m.p. °C. | Recrystallization Solvent |
|---|---|---|
| $CH_3CH_2CH_2-$ | 142-144 | Ethanol |
| $CH_2=CHCH_2-$ | 130-133 | Methanol/Ethyl Acetate |
| $HOCH_2CH_2CH_2-$ | 148-151 | Ethanol |

EXAMPLE 12

A mixture of cyclohexylamine (4 ml.), pyridine (6 ml.) and 2-guanidino-4-[2-(3-cyano-2-methylisothioureido)ethylthiomethyl]thiazole (1 g.) was allowed to stand at room temperature for 2 weeks. The mixture was evaporated to dryness and the residaul crude free base was converted to the hydrogen maleate salt. This was recrystallized from methanol/ether to give 2-guanidino-4-[2-(2-cyano-3-cyclohexylguanidino)ethylthiomethyl]thiazole hydrogen maleate, m.p. 156°-159° C.

EXAMPLE 13

Acetic anhydride (0.39 g.) was added to a stirred suspension of 2-guanidino-4-[2-(2-cyano-3-methylguanidino)ethylthiomethyl]thiazole (1.10 g.) in pyridine (6 ml.) at room temperature. After stirring for two hours, the mixture was diluted with water (50 ml.), extracted with methylene chloride (3×30 ml.) and the combined extracts washed with water (100 ml.) and dried over magnesium sulphate. The solution was filtered and evaporated to dryness to leave a gum which was purified by column chromatography (silica column, eluted with ethyl acetate/ethanol/ammonia (s.g. 0.880) 6:1:1 v/v/v) to give 2-(2-acetylguanidino)-4-[2-(2-cyano-3-methylguanidino)ethylthiomethyl]thiazole as an amorphous solid. The n.m.r. spectrum in $d_6$ dimethyl sulphoxide using tetramethylsilane as internal standard had the following resonances (δ): 2.1 (3H, singlet); 2.7 (5H, multiplet); 3.3 (multiplet, obscured by $H_2O$); 3.7 (2H. singlet); 6.8 (1H, singlet); 7.0 (2H, broad multiplet; 9.0 (2H, very broad) and 10.7 (1H, broad).

In a similar manner, reaction with propionic anhydride gave 2-(3-propionylguanidino)-4-[2-(2-cyano-3-methylguanidino)ethylthiomethyl]thiazole as a gum. The n.m.r. spectrum in $d_6$ dimethyl sulphoxide using tetramethylsilane as internal standard had the following resonances (δ): 1.1 (3H, triplet); 2.4 (2H, quartet); 2.6 (2H, triplet); 2.8 (3H, doublet); 3.3 (2H, triplet); 3.7 (2H, singlet); 6.55 and 6.60 (overlapping singlets); 8.9 and 9.5 (broad).

EXAMPLE 14

A solution of benzoic anhydride (0.73 g.) in pyridine (5 ml.) was added to a stirred suspension of 2-guanidino-4-[2-(2-cyano-3-methylguanidino)ethylthiomethyl]thiazole (1.0 g.) in pyridine (5 ml.). The mixture was stirred for 24 hours, diluted with water (50 ml.) and the resulting white suspension filtered. The residual white solid was recrystallized first from aqueous methanol and then from acetone/cyclohexane to give 2-(2-benzoylguanidino)-4-[2-(2-cyano-3-methylguanidino)ethylthiomethyl]thiazole, m.p. 179°-181° C.

EXAMPLE 15

A mixture of 2-(2-acetylguanidino)-4-[2-(2-cyano-3-methylguanidino)ethylthiomethyl]thiazole (13.6 mg.), methanol (1 ml.) and 0.2 N aqueous sodium hydroxide solution (2 ml.) was stirred at room temperature for 20 minutes. This resulted in complete conversion to 2-guanidino-4-[2-(2-cyano-3-methylguanidino)ethylthiomethyl]thiazole, identical with the free base of the product obtained in Example 3. The free base had a m.p. 159°-161° C. on recrystallization from aqueous dimethylformamide.

EXAMPLE 16

A mixture of 2-(2-benzoylguanidino)-4-[2-(2-cyano-3-methylguanidino)ethylthiomethyl]thiazole (10.7 mg.), methanol (1 ml.) and 1 N aqueous sodium hydroxide solution (2 ml.) was stirred overnight at room temperature. The product was 2-guanidino-4-[2-(2-cyano-3-methylguanidino)ethylthiomethyl]thiazole, identical with the free base of the product obtained in Example 3. The free base had a m.p. 159°-161° C. on recrystallization from aqueous dimethylformamide.

EXAMPLE 17

A mixture of dimethyl (toluene-p-sulphonylimido)dithiocarbonate (0.90 g.), a triethylamine (0.69 g.), ethanol (10 ml.) and 2-guanidino-4-(2-aminoethylthiomethyl)-thiazole dihydrochloride (1.0 g.) was stirred at room temperature for two hours and left to stand for three days. An ethanolic solution of methylamine (33% w/v; 3 ml.) was added and the mixture left to stand for three days. The mixture was evaporated to dryness. The residue was converted to the hydrogen maleate salt which was recrystallized from water to give 2-guanidino-4-[2-(2-toluene-p-sulphonyl-3-methylguanidino)ethylthiomethyl]thiazole hydrogen maleate, m.p. 167°–170° C.

EXAMPLE 18

A mixture of 2-(2-n-butylguanidino)-4-(2-aminoethyl)thiomethylthiazole hydrochloride (1.10 g.), methylisothiocyanate (0.70 g.), triethylamine (0.90 g.) and methanol (5 ml.) was stirred at room temperature for four hours. It was then diluted with water (25 ml.), extracted with ethyl acetate (2×25 ml.) and the combined extracts washed with water (50 ml.). The organic layer was then extracted with 1 N hydrochloric acid (2×25 ml.), the combined aqueous layers washed with ethyl acetate (25 ml.) and then basified by addition of aqueous ammonia. The resulting emulsion was extracted with ethyl acetate and the extract was washed with water and dried over magnesium sulphate. It was filtered and evaporated to dryness to give 2-(2-n-butylguanidino)-4-[2-(3-methylthioureido)ethylthiomethyl]-thiazole as a brown gum. The n.m.r. spectrum in $d_6$ dimethyl sulphoxide (DMSO) using tetramethylsilane as internal standard had the following resonances ($\delta$): 0.6–1.5 (7H, multiplet); 2.5 (2H, multiplet); 2.75 (3H, triplet); 3–3.5 (4H, multiplet); 3.55 (2H, singlet); 6.45 (1H, singlet); 6.7–7.6 (broad multiplet).

The 2-(2-n-butylguanidino)-4-(2-aminoethyl)thiomethylthiazole hydrochloride used as starting material may be prepared as follows:

A solution of 1,3-dichloroacetone (3.02 g.) in acetone (10 ml.) was added to a stirred suspension of (N-n-butylamidino)thiourea (4.04 g.) in acetone (25 ml.) at room temperature. The resulting clear pale yellow solution was stirred for three days, then cooled in ice, and the precipitated solid filtered off and washed with acetone to give 2-(2-n-butylguanidino)-4-chloromethylthiazole hydrochloride A solution of 2-aminoethanethiol hydrochloride (1.85 g.) in ethanol (30 ml.) was added to a stirred solution of sodium (0.90 g.) in ethanol (50 ml.) under a nitrogen atmosphere. A solution of 2-(2-n-butylguanidino)-4-chloromethylthiazole hydrochloride (2.20 g.) in ethanol (50 ml.) was added dropwise to the mixture, which was then stirred for 3 hours while warming to room temperature. A mixture of concentrated hydrochloric acid (5 ml.) and water (15 ml.) was then added, and the mixture evaporated to dryness. The residual gummy solid was extracted with boiling ethanol (3×20 ml.) and the residual white solid discarded. The combined ethanolic extracts were filtered and the filtrate evaporated to dryness to give 2-(2-n-butylguanidino)-4-(2-aminoethyl)thiomethylthiazole hydrochloride as a thick gum which was used without further purification.

EXAMPLE 19

A suspension of 2-guanidino-4-[2-(2-cyano-3-methylguanidino)ethylthiomethyl]thiazole (0.614 g.) in aqueous methanol (120 ml. water, 20 ml. methanol) was treated with sodium metaperiodate (0.440 g.) and stirred at room temperature for 16 hours. The solution was evaporated to dryness and n-propanol added to the residue and the suspension evaporated to dryness on a rotary evaporator. The residue was boiled with ethanol and filtered. The residual solid was dissolved in methanol (10 ml.) and added to an acetone solution of maleic acid. The resulting precipitate was filtered and washed with methanol to give 2-guanidino-4-[2-(2-cyano-3-methylguanidino)ethylsulphinylmethyl]thiazole hydrogen maleate, m.p. 205°–210° C.

EXAMPLE 20

To a stirred solution of diethyl (N-cyanoimido)carbonate (1.59 g.) in ethanol (15 ml.) at room temperature was added a solution of 2-guanidino-4-[(2-aminoethyl)-thiomethyl]thiazole (2.58 g.) in ethanol (25 ml.) over 15 minutes with sufficient cooling to maintain the temperature at about 20° C. The solution was stirred at room temperature for a further 30 minutes and then more diethyl (N-cyanoimido)carbonate (0.318 g.) in ethanol (3 ml.) was added. The solution was stirred at room temperature for 15 minutes and then evaporated to dryness under reduced pressure to give a pale yellow paste. This residue was dissolved in ethyl acetate (20 ml.) and the solution was washed with water (20 ml., 2×10 ml.) then dried (magnesium sulphate) and evaporated under reduced pressure to give 2-guanidino-4-[2-(3-cyano-2-ethylisoureido)ethylthiomethyl]thiazole containing a small amount of ethyl acetate. The n.m.r. spectrum in $CDCl_3$ using tetramethylsilane as internal standard had the following resonances ($\delta$): 6.5 (5H, very broad); 6.4 (1H, singlet); 4–4.5 (obscured by ethyl acetate); 3.6 (2H, singlet); 3.4 (2H, multiplet); 2.7 (2H, multiplet); 2.0 (ethyl acetate); 1.2–1.5 (obscured by ethyl acetate).

EXAMPLE 21

A mixture of 2-guanidino-4-[4-(3-cyano-2-ethylisoureido)ethylthiomethyl]thiazole (0.540 g.) and 25–30% w/v aqueous methylamine (3.5 ml.) was stirred under a nitrogen atmosphere at 105°–110° C. for 33 minutes then cooled to room temperature. The addition of water (2.0 ml.) to the clear solution caused an orange gum to deposit. The mixture was stirred in ice for 30 minutes, then allowed to stand overnight at room temperature. The off-white solid (0.229 g.) was collected, washed with water (2 ml.) and dried at 60° for 2 hours then recrystallized from aqueous dimethylformamide to give 2-guanidino-4-[2-(2-cyano-3-methylguanidino)ethylthiomethyl]thiazole, m.p. 159°–161° C.

EXAMPLE 22

Triethylamine (2.02 g.) was added to a suspension of 2-guanidino-4-[(2-aminoethyl)thiomethyl]thiazole dihydrochloride (3.04 g.) in methanol (30 ml.) stirred at room temperature. Dimethyl (N-cyanoimido)carbonate (1.14 g.) was added and the mixture was stirred at room temperature for 3 hours and then evaporated under reduced pressure. The residue was extracted with ethyl acetate (35 ml.) and the solution was washed with water (25 ml., 10 ml.) then dried (magnesium sulphate) and evaporated under reduced pressure to give 2-guanidino-4-[2-(3-cyano-2-methylisoureido)ethylthiomethyl]-thiazole (2.16 g.). The n.m.r. spectrum in $CDCl_3/d_6$ dimethyl sulphoxide using tetramethylsilane as internal standard had the following resonances ($\delta$): 7.7 (1H, very broad); 6.7 (4H, broad); 6.4 (1H, singlet); 3.8 (3H, singlet); 3.6 (2H, singlet); 3.4 (obscured by H₂O); 2.7 (2H, broad triplet).

EXAMPLE 23

A mixture of 2-guanidino-4-[2-(3-cyano-2-methylisoureido)ethylthiomethyl]thiazole (1.88 g.) and 30% w/v aqueous methylamine (6.0 ml.) was stirred together at room temperature. After 1 hour 40 minutes water (20 ml.) was added, and stirring was continued for 15 minutes. The white solid (1.265 g.) was collected, washed with water (3 ml.) and dried in vacuo overnight. Recrystallization from aqueous dimethylformamide gave 2-guanidino-4-[2-(2-cyano-3-methylguanidino)ethylthiomethyl]thiazole, m.p. 160°–161.5° C.

EXAMPLE 24

A solution of 2-guanidino-4-[(2-aminoethyl)thiomethyl]thiazole hydrochloride (3.34 g.) in ethanol (30 ml.) and triethylamine (2.22 g.) was treated with 1-methoxycarbonyl-2-methylisothiourea (1.61 g.) and the resulting solution stirred for 48 hours at room temperature. The solution was evaporated and the residue taken up into a small volume of ethanol and filtered. The ethanol solution was added to an acetone solution of maleic acid and the precipitate filtered after standing for 2 hours. Two recrystallizations from ethanol gave 2-guanidino-4-[2-(2-methoxycarbonylguanidino)ethylthiomethyl]-thiazole di(hydrogen maleate), m.p. 173°–175° C.

EXAMPLE 25

A solution of 2-guanidino-4-[2-(3-methylthioureido)ethylthiomethyl]thiazole hydrogen maleate (0.42 g.) in ethanol (15 ml.) was treated with methyl iodide (0.175 g.). The clear solution was heated under reflux on a steam bath for 1.5 hours, cooled and the volume reduced to 5 ml. by evaporation under reduced pressure. The insoluble material was filtered and recrystallized from ethanol to give 2-guanidino-4-[2-(2,3-dimethylisothioureido)ethylthiomethyl]thiazole hydrogen maleate hydriodide. Found: C, 30.2; H, 4.1; N, 14.8; S, 17.2. C₁₄H₂₃IN₆O₄S₃ requires C, 29.94; H, 4.09; N, 14.97; S, 17.11%

A solution of 2-guanidino-4-[2-(2,3-dimethylisothioureido)ethylthiomethyl]thiazole hydrogen maleate hydriodide (0.8 g.) in water (10 ml.) was treated with an aqueous solution of potassium carbonate (0.3 g. in 5 ml. water) and the solution heated on the steam bath for 4 hours. After cooling and allowing to stand for 16 hours the aqueous layer was decanted from the brown gum and the gum taken up into ethanol and filtered. The filtrate was evaporated to dryness and the residue converted to the hydrogen maleate salt which was recrystallized from ethanol to give 2-guanidino-4-[2-(3-methylureido)ethylthiomethyl]thiazole hydrogen maleate hemihydrate, m.p. 167°–170° C.

The following Examples are provided as a means of illustrating how further compounds falling within the scope of this invention may, if desired, be prepared.

EXAMPLE 26

By reaction of 2-guanidino-4-[(2-aminoethyl)thiomethyl]thiazole and 1,2-dimethoxycyclobutene-3,4-dione there may be prepared 1-[2-(2-guanidinothiazol-4-yl)ethylthiomethylamino]-2-methoxycyclobutene-3,4-dione.

By reaction of this product with methylamine in ethanol or an excess of n-hexylamine, allylamine, cyclohexylamine, 2-hydroxyethylamine, 2-methoxyethylamine or 2-dimethylaminoethylamine, the following compounds may be prepared:

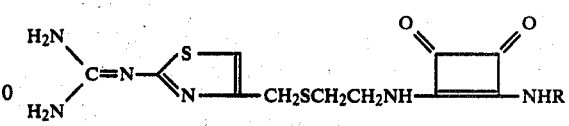

wherein R is methyl, n-hexyl, allyl, cyclohexyl, 2-hydroxyethyl, 2-methoxyethyl and 2-dimethylaminoethyl.

EXAMPLE 27

By reaction of 2-guanidino-4-[(2-aminoethyl)thiomethyl]thiazole with 1-methylthio-1-methylsulphinyl-2-nitroethylene followed by reaction of the product with ethanolic methylamine there may be prepared 1-[2-(2-guanidinothiazol-4-yl)ethylthiomethylamino]-1-methylamino-2-nitroethylene.

EXAMPLE 28

By reaction of 2-guanidino-4-[(2-aminoethyl)thiomethylthiazole with 1,1-dicyano-2-methylamino-2-methylthioethylene there may be prepared 1-[2-(2-guanidinothiazol-4-yl)ethylthiomethylamino]-1-methylamino-2,2-dicyanoethylene.

EXAMPLE 29

By reaction of 2-guanidino-4-[(2-aminoethyl)thiomethyl]-5-bromothiazole (which may itself be prepared by bromination of 2-guanidino-4-[(2-aminoethyl)thiomethyl]thiazole) with methylisothiocyanate there may be prepared 2-guanidino-5-bromo-4-[2-(3-methylthioureido)ethylthiomethyl]thiazole.

EXAMPLE 30

By reaction of 2-guanidino-4-[(2-aminoethyl)thiomethyl]-5-methylthiazole with methylisothiocyanate there may be prepared 2-guanidino-5-methyl-4-[2-(3-methylthioureido)ethylthiomethyl]thiazole.

The starting material may be prepared by reaction of 1,3-dichlorobutan-2-one with amidinothiourea followed by reaction of the product with 2-aminoethanethiol.

As noted above, the guanidine derivatives of the invention are a histamine H-2 antagonist, inhibit the secretion of gastric acid in warm-blooded animals and are therefore useful in the treatment of peptic ulcers and other conditions caused or exacerbated by gastric acidity, such as stress ulceration or gastric intestinal bleeding due to trauma.

The histamine H-2 antagonist activity may be demonstrated on standard tests, for example by the ability of the compound of the formula I to inhibit the histamine-induced positive chronotropic response in the spontaneously beating right atrium of the guinea pig heart or by its ability to inhibit the histamine-induced increase in the level of cyclic AMP (3,5-adenosine monophosphate), in the presence of a phosphodiesterase inhibitor, in a free cell suspension obtained from canine gastric mucosa.

The guinea pig heart atrium test is carried out as follows:

A guinea pig right atrium is suspended at 1 g. tension (isometric) in a thermostatically controlled (30° C.)

tissue bath (25 ml.) containing oxygenated (95% $O_2$; 5% $CO_2$) Krebs-Hanseleit buffer (pH 7.4). The tissue is allowed to stabilize over 1 hour during which time it is washed 2-4 times. Individual contractions are recorded with a force-displacement transducer through a strain gauge coupler, and instantaneous rates are monitored with a cardiotachometer. A control response to 1 micromole histamine in the above described tissue bath is obtained after which the tissue is washed 3 times and allowed to re-equilibrate to basal rate. After re-equilibration for 15 minutes, the test compound is added to the tissue bath at the desired final concentration. Ten minutes after addition of the compound, a fresh histamine (1 micromole) bath solution is again added to the tissue bath containing the test compound. Then the response to histamine in the presence of antagonist is compared to the histamine control response. The result is expressed as a percentage of the histamine control response. Thereafter, the apparent dissociation constant of the H-2 antagonist is determined by standard procedures.

All the compounds exemplified in this specification, with the exception of 2-guanidino-4-[2-(2-cyano-3-methylguanidino)ethylsulphinylmethyl]thiazole (Example 19) are active on the guinea pig heart atrium test at or below a bath concentration of 10 micromoles, and the more active compounds show complete inhibition of response at this concentration.

The inhibition of the secretion of gastric acid may be demonstrated in standard tests, for example by the ability of the compound of the formula I, when dosed intravenously, intragastrically or orally, to inhibit the secretion of acidic gastric juice in, for example, rats, or cats or dogs provided with gastric fistulae and whose gastric secretion is stimulated by the administration of a secretagogue, for example pentagastrin or histamine.

The test in dogs in carried out as follows:

A female pure bred beagle (9-12 kg.) having a chronic gastric fistula is fasted overnight with water ad lib. During the experiment the dog is lightly restrained in a standing position. When studying the test compound by the intravenous route, the fistula is opened and, after ascertaining the absence of secretion over a period of 30 minutes, a continuous intravenous infusion of secretagogue (0.5 micromole/kg./hour of histamine or 2 micrograms/kg./hour pentagastrin) in saline (15ml/hour) is begun. Gastric acid samples are collected every 15 minutes. The volume of each sample is measured and a 1 ml. aliquot is titrated to neutrality with 0.1 N NaOH to determine acid concentration. When a plateau of secretion is reached (1-2 hours), the test compound is administered intravenously in saline and gastric acid samples are collected for a further 2-3 hours during which time the infusion of secretagogue continues uninterrupted.

When studying the test compound by the intragastric route, the absence of secretion over a period of 30 minutes is ascertained and the test compound, contained in 25 ml. of 0.5% w/v hydroxypropyl methylcellulose and 0.1% w/v TWEEN 80 polyoxyethylene(20) sorbitan monooleate in water (TWEEN is a trademark of ICI Americas Inc.), is instilled into the stomach through a fistula dosing plug. One hour later, the fistula is reopened and intravenous infusion of a secretagogue, as described above, is immediately begun. Gastric acid samples are measured as described above and the approach of acid secretion to a plateau is compared to that of a control animal which is dosed intragastrically only with the dosing vehicle.

When studying the test compound by the oral route, it is administered in a gelatin capsule washed down with 15 ml. of water. One hour later, the fistula is opened and intravenous infusion of the secretagogue is immediately begun. Gastric acid samples are measured as above and the approach of acid secretion to a plateau is compared to that of an undosed control animal.

In all but one case the results obtained in the heart atrium test are predictive of activity in the dog test. The exception is 2-quanidino-4-[2-(2-cyano-3-methylguanidino)ethylsulphinylmethyl]thiazole (Example 19) which is inactive at 10 micromoles in the atrium test but inhibits acid secretion in the dog test when dosed intragastrically.

No overt toxicity or side effects were noted with any of the compounds during the dog tests. The following compounds, chosen at random from among the compounds exemplified in this specification, showed no overt toxicity when dosed intraperitoneally to groups of 4 or 5 mice at the dose indicated.

$$\underset{H_2N}{\overset{R^2NH}{\diagdown}}C=N-\underset{N}{\overset{S}{\diagup}}\underset{}{\overset{H}{\diagdown}}CH_2-Y-(CH_2)_n-\overset{Z}{\overset{\|}{N}}HCNHR^5$$

| n | Y | Z   | $R^2$ | $R^5$      | Dose (mg./kg.) |
|---|---|-----|-------|------------|----------------|
| 2 | S | S   | H     | $CH_3$     | 73             |
| 2 | S | NCN | H     | $CH_3$     | 100            |
| 2 | S | NCN | H     | $CH_3CH_2$ | 100            |

According to a further feature of the invention there is provide a pharmaceutical composition which comprises a guanidine derivative of the invention in association with a non-toxic pharmaceutically acceptable diluent or carrier.

The pharmaceutical composition may, for example, be in a form suitable for oral, rectal, parenteral or topical administration, for which purposes it may be formulated by means known to the art into the form of, for example, tablets, capsules, aqueous or oily solutions or suspensions, emulsions, dispersible powders, suppositories, sterile injectable aqueous or oily solutions or suspensions, gels, creams, ointments or lotions.

In addition to the guanidine derivatives of formula I, the pharmaceutical composition of the invention for oral, rectal or parenteral administration may also contain, or be co-administered with, one or more known drugs selected from antacids, for example aluminum hydroxide-magnesium hydroxide mixtures; antipepsin compounds, for example pepstatin; other histamine H-2 antagonists, for example cimetidine; ulcer healing agents, for example dihydrocanadensolide, carbenoxolone or bismuth salts; anti-inflammatory agents, for example ibuprofen, indomethacin, naproxen or aspirin; prostaglandins, for example 16,16-dimethyl-prostaglandin $E_2$; classical antihistamines (histamine H-1 antagonists), for example pyrilamine or diphenhydramine; anticholinergic agents, for example atropine or propantheline bromide; anxiolytic agents, for example diazepam, chlordiazepoxide or phenobarbital.

The pharmaceutical composition of the invention for topical administration may also contain, in addition to the guanidine derivative, one or more classical antihistamines (histamine H-1 antagonists), for example pyrilamine or diphenhydramine and/or one or more steroidal anti-inflammatory agents, for example fluocinolone or triamcinolone. A topical formulation may contain 1–10% w/w of the guanidine derivative of the invention.

A preferred pharmaceutical composition of the invention is one suitable for oral administration in units dosage form, for example a tablet or capsule which contains between 10 mg. and 500 mg. of the guanidine derivative, or one suitable for intravenous, subcutaneous or intramuscular injection, for example a sterile aqueous solution containing between 0.1% and 10% w/w of the guanidine derivative.

Examples of formulations for preparing tablets, capsules, liquids, parenterals, and suppositories containing the guanidine derivatives of the present invention are described below. It will be recognized by one skilled in the present art that other known methods of preparing such pharmaceutical compositions can be used and obviously the size of the tablet or capsule or the strength of the dosage form may be suitably varied in order to satisfy the particular requirements, such as dosage level indicated. Any of the well-known suitable pharmaceutical carriers can be used to prepare acceptable dosage forms so as to provide an effective amount or therapeutically effective amount of the compound to be administered.

| Tablet Containing 50 mg. of 2-guanidino-4-[2-(2-cyano-3-ethylguanidino)ethylthiomethyl]thiazole | 1000 Tablets (Grams) |
| --- | --- |
| 2-guanidino-4-[2-(2-cyano-3-ethylguanidino)-ethylthiomethyl]thiazole | 50 |
| Starch | 102 |
| Powdered Lactose | 102 |
| Talc | 26 |
| Weight of Granulation | 280 |

Combine all ingredients, mix, and then compress into slugs. The slugs should then be ground to form granules that will pass through a 14 to 16 mesh screen. The granules may then be recompressed into tablets using a suitable compression mold to form tablets, each weighing 280 mg.

| Capsule Containing 100 mg. of 2-guanidino-4-[2-(2-cyano-3-methylguanidino)ethylthiomethyl]thiazole | |
| --- | --- |
| 2-guanidino-4-[2-(2-cyano-3-methylguanidino)-ethylthiomethyl]thiazole | 100 mg. |
| Powdered Lactose | 200 mg. |
| D.T.D. Capsules No. 1000 | |

Mix the ingredients so as to evenly distribute the active ingredient throughout the lactose. Pack the powder into a No. 1 empty gelatin capsule.

| Suspension Containing 50 mg. per 5 cc. of 2-guanidino-4-[2-(2-cyanoguanidino)ethylthiomethyl]thiazole hydrochloride | |
| --- | --- |
| 2-guanidino-4-[2-(2-cyanoguanidino)ethylthiomethyl]thiazole hydrochloride | 10 grams |
| Tragacanth | 50 grams |
| Amaranth | 10 grams |
| Syrup Wild Cherry | 60 ml. |
| Distilled Water q.s. | 1000 ml |

Hydrate the tragacanth with sufficient water to form a smooth paste and to this add the 2-quanidino-4-[2-(2-cyanoguanidino)ethylthiomethyl]thiazole hydrochloride, followed by the amaranth which has been previously dissolved in water. Then add the syrup of wild cherry and add distilled water to make 1000 ml.

| Injectable Containing 5 mg. of 2-guanidino-4-[2-(2-nitroguanidino)ethylthiomethyl]thiazole hydrochloride Per Milliliter | |
| --- | --- |
| 2-guanidino-4-[2-(2-nitroguanidino)ethylthiomethyl]thiazole hydrochloride | 5.0 grams |
| Chlorobutanol | 3.0 grams |
| Propylene Glycol | 20.0 ml. |
| Water for Injection q.s. | 1000.0 ml. |

Combine the above ingredients, clarify by filtration, fill into vials, seal, and sterilize.

| Suppository Containing 200 mg. of 2-guanidino-4-[2-(3-methylureido)ethylthiomethyl]thiazole | |
| --- | --- |
| 2-guanidino-4-[2-(3-methylureido)-ethylthiomethyl]thiazole | 0.2 gram |
| Cocoa butter | 1.8 grams |
| Make of Such No. 100 | |

Melt cocoa butter and disperse the 2-guanidino-4-[2-(3-methylureido)ethylthiomethyl]thiazole in the molten mass and stir until uniform. Pour the resulting molten mass into suppository mold and chill. Remove suppositories from mole and package.

| Cream Containing 5% w/w of 2-guanidino-4-[2-(2-nitroguanidino)ethylthiomethyl]thiazole hydrogen maleate | |
| --- | --- |
| 2-guanidino-4-[2-(2-nitroguanidino)ethylthiomethyl]thiazole hydrogen maleate | 5 grams |
| Cold Cream | 95 grams |

Disperse 2-guanidino-4-[2-(2-nitroguanidino(ethylthiomethyl]thiazole hydrogen maleate in 5 ml. water and blend into the cold cream. Grind the resulting mixture to obtain a uniform and smooth product.

Evaluation in laboratory animals indicates that the present guanidine derivatives or compounds can be used to inhibit the secretion of gastric acid when administered in a therapeutically effective amount to a living, warmblooded animal in need of treatment for peptic ulcers and other conditions caused or exacerbated by gastric acidity. The effectiveness and dosage required vary, as is customary in this art, with the species being treated, particular disorder being treated, weight of the animal, and the route of administration. In accordance with the present invention, the subject compounds can be used in living animals, for example dogs,, in need of such treatment at doses from about 0.03 milligram to 30 milligrams per kilogram body weight (for example 3 mg./kg.) as needed, generally 2 to 4 times a day. A more preferred dose, in view of optimum results and low dosage, is from about 0.3 milligram to 3 milligrams per kilogram body weight (for example 1 mg./kg.) as needed, generally 2 to 4 times a day.

The compounds or pharmaceutical compositions of the invention will normally be administered to humans for the treatment of peptic ulcers and other conditions caused or exacerbated by gastric acidity in the same general manner as that employed for cimetidine, due allowance being made in terms of dose levels for the potency of the guanidine derivative of the present invention relative to cimetidine. Thus eac human patient will receive an oral dose of between 15 mg. and 1500 mg. and preferably between 20 mg. and 200 mg. of a quanidine derivative of the present invention (for example, 50 mg. orally for an adult human) or an intravenous, subcutaneous or intramuscular dose of between 1.5 mg. and 150 mg., and preferably between 5 mg. and 20 mg. of a guanidine derivative of the present invention, the subject guanidine derivative being administered 2 to 4 times per day. The rectal dose will be approximatey the same as the oral dose. The composition may be administered less frequently when it contains an amount of guanidine derivative which is a multiple of the amount which is effective when given 2–4 times per day.

What we claim is:

1. A guanidine derivative of the formula:

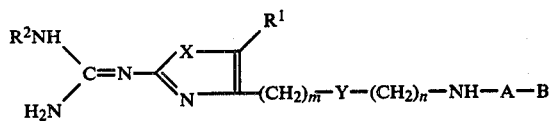

in which X is a sulphur atom or NH radical; Y is an oxygen or sulphur atom or a sulphinyl radical; m is 1 to 4 and n is 1 to 4, provided that when Y is an oxygen atom or a sulphinyl radical n is 2 to 4; $R^1$ is a hydrogen or halogen atom or an alkyl radical of 1 to 6 carbon atoms; $R^2$ is a hydrogen atom, an alkyl radical of 1 to 10 carbon atoms, an alkanoyl radical of 1 to 6 carbon atoms or an aroyl radical of 7 to 11 carbon atoms; A is a 3,4-dioxocyclobuten-1,2-diyl radical or a radical of the formula C=Z in which Z is an oxygen or sulphur atom or a radical of the formula NCN, $NNO_2$, $CHNO_2$, $NCONH_2$, $C(CN)_2$, $NCOR^3$, $NCO_2R^3$, $NSO_2R^3$ or $NR^4$ in which $R^3$ is an alkyl radical of 1 to 6 carbon atoms or an aryl radical of 6 to 12 carbon atoms and $R^4$ is a hydrogen atom or an alkyl radical of 1 to 6 carbon atoms; B is an alkoxy or alkylthio radical of 1 to 6 carbon atoms or a radical of the formula $NR^5R^6$ in which $R^5$ and $R^6$, which may be the same or different, are hydrogen atoms, alkyl radicals of 1 to 10 carbon atoms, alkenyl radicals of 3 to 10 carbon atoms in which the double bond is separated from the nitrogen atom of $NR^5R^6$ by at least one carbon atom, cycloalkyl radicals of 3 to 8 carbon atoms, (primary hydroxy)alkyl radicals of 2 to 6 carbon atoms in which the oxygen atom is separated from the nitrogen atom of $NR^5R^6$ by at least two carbon atoms, alkoxyalkyl radicals of 3 to 10 carbon atoms in which the oxygen atom is separated from the nitrogen atom of $NR^5R^6$ by at least two carbon atoms, alkylaminoalkyl radicals of 3 to 10 carbon atoms in which the nitrogen atom is separated from the nitrogen atom of $NR^5R^6$ by at least two carbon atoms; or dialkylaminoalkyl radicals of 4 to 10 carbon atoms in which the nitrogen atom is separated from the nitrogen atom of $NR^5R^6$ by at least two carbon atoms; and the pharmaceutically acceptable acid-addition salts thereof.

2. A compound of claim 1 wherein X is a sulphur atom or an NH radical; Y is a sulphur atom or a sulphinyl radical; m is 1 to 4 and n is 1 to 4, provided that when Y is a sulphinyl radical n is 2 to 4; $R^1$ is a hydrogen or bromine atom or methyl radical; $R^2$ is a hydrogen atom, or a methyl, n-butyl, acetyl, propionyl or benzoyl radical; A is a 3,4-dioxocyclobuten-1,2-diyl radical or a radical of the formula C=Z in which Z is an oxygen or sulphur atom or a radical of the formula NCN, $NNO_2$, $CHNO_2$, $NCONH_2$, $C(CN)_2$, $NCO_2CH_3$, $NSO_2$-p-tolyl or $NCH_3$; B is a methoxy, ethoxy or methylthio radical or a radical of the formula $NR^5R^6$ in which $R^5$ and $R^6$ are independently selected from the group consisting of methyl, ethyl, n-propyl, isopropyl, n-hexyl, allyl, cyclohexyl, 2-hydroxyethyl, 3-hydroxypropyl, 2-methoxyethyl and 2-dimethylaminoethyl radicals.

3. A compound of claim 1 wherein X is a sulphur atom.

4. A compound of claim 3 wherein Y is a sulphur atom.

5. A compound of claim 4 wherein $R^1$ is a hydrogen atom.

6. A compound of claim 5 were $R^2$ is a hydrogen atom.

7. A compound of claim 6 where A is C=Z wherein Z is NCN.

8. A compound of claim 7 where B is $NR^5R^6$ wherein $R^5$ is methyl and $R^6$ is methyl.

9. A compound of claim 1 where X is a sulphur atom; Y is a sulphur atom; m is 1 to 4; n is 1 to 4; $R^1$ is a hydrogen atom; $R^2$ is a hydrogen atom or a methyl rdical; A is C=Z wherein Z is a sulphur atom or a radical of the formula NCN, $NNO_2$, $NCONH_2$, $NCOR^3$, $NCO_2R^3$ or $NSO_2R^3$ in which $R^3$ is a phenyl radical; and B is a radical of the formula $NR^4R^5$ wherein $R^4$ and $R^5$ are independently selected from the group consisting of hydrogen and lower alkyl radicals of 1 to 4 carbon atoms.

10. A compound of claim 1 where X is a sulphur atom; Y is a sulphur atom; m is 1 to 4; n is 1 to 4; $R^1$ is hydrogen; $R^2$ is hydrogen; A is C=Z where Z is a sulphur atom or a radical of the formul NCN; and B is a radical of the formula $NR^4R^5$ wherein $R^4$ and $R^5$ are independently selected from the group consisting of hydrogen and lower alkyl radicals of 1 to 4 carbon atoms.

11. A compound of claim 4 where m is 1 and n is 1 to 2.

12. A compound of claim 1 which is 2-quanidino-4-[2-(2-cyano-3-ethylguanidino)ethylthiomethyl]thiazole.

13. A compound of claim 1 which is 2-guanidino-4-[2-(2-cyano-3-methylguanidino)ethylthiomethyl]thiazole.

14. A compound of claim 1 which is 2-guanidino-4-[2-(2-nitroguanidino)ethylthiomethyl]thiazole.

15. A compound of claim 1 which is 2-guanidino-4-[2-(2-cyanoguanidino)ethylthiomethyl]thiazole.

16. A compound of claim 1 which is 2-guanidino-4-[2-(2-cyano-3-(2-hydroxyethyl)guanidino)ethylthiomethyl]thiazole.

17. A pharmaceutical composition to inhibit gastric acid secretion comprising a therapeutically effective amount of a compound of claim 1 to inhibit said secretion in a pharmaceutical carrier.

18. A pharmaceutical composition to inhibit gastric acid secretion comprising a therapeutically effective amount of a compound of claim 13 to inhibit said secretion in a pharmaceutical carrier.

19. A method of inhibiting gastric acid secretion in a living animal comprising administering to the animal a composition of claim 17.

* * * * *

UNITED STATES PATENT AND TRADEMARK OFFICE
CERTIFICATE OF CORRECTION

PATENT NO. : 4,165,378

DATED : August 21, 1979

INVENTOR(S) : David J. Gilman, James M. Wardleworth, Tobias O. Yellin

It is certified that error appears in the above-identified patent and that said Letters Patent are hereby corrected as shown below:

[73] "Assignee: " ICI Americas Inc., Wilmington, Delaware" should read --Assignees: Imperial Chemical Industries Limited, Millbank, London, England and ICI Americas Inc., Wilmington, Delaware--.

Col. 2, line 24 - "o" should read --or--.

Col. 8, line 13 - "ot" should read --out--.

Col. 10, line 8 - "slid" should read --solid--.

Col. 11, line 36 - "(1H, singlet;" should read --(1H, singlet);--.

Col. 13, line 29 - "crystallized" should read --recrystallized--.

Col. 14, line 22 - "7.0(2H, broad multiplet;" should read --7.0(2H, broad multiplet);--.

UNITED STATES PATENT AND TRADEMARK OFFICE
CERTIFICATE OF CORRECTION

PATENT NO. : 4,165,378
DATED : August 21, 1979
INVENTOR(S) : David J. Gilman, James M. Wardleworth, Tobias O. Yellin It is certified that error appears in the above-identified patent and that said Letters Patent are hereby corrected as shown below:

Col. 18, line 27 - "thylthiazole" should read --thyl] thiazole--.

Col. 20, line 36 - "provide" should read --provided--.

Col. 22, line 68 - "eac" should read --each--.

Col. 24, line 15 - "were" should read --where--.

Col. 24, line 24 - "rdical" should read --radical--.

Under Foreign Application Priority Data should read

--[30] Foreign Application Priority Data
April 20, 1977   United Kingdom.......16389/77--

Signed and Sealed this

Eleventh Day of December 1979

[SEAL]

Attest:

SIDNEY A. DIAMOND

Attesting Officer

Commissioner of Patents and Trademarks